United States Patent [19]
Gallegos

[11] Patent Number: 4,849,863
[45] Date of Patent: Jul. 18, 1989

[54] SAFETY LIGHT AND SWEAT BELT

[76] Inventor: Rodney T. Gallegos, 3135 Ogden Ave., Ogden, Utah 84403

[21] Appl. No.: 189,030

[22] Filed: May 2, 1988

[51] Int. Cl.⁴ ............................................. F21L 15/20
[52] U.S. Cl. ......................................... 362/108; 2/11; 2/311; 2/338
[58] Field of Search ............ 362/103, 108; 128/25 R, 128/58, 63, 61, 62 R; 450/94, 97, 154; 272/119, 143; 2/311, 11, 338, 312

[56] References Cited
U.S. PATENT DOCUMENTS

| 1,217,666 | 2/1917 | Thulin | 362/103 |
|---|---|---|---|
| 1,662,668 | 3/1928 | Gossett | 362/103 |
| 1,860,202 | 5/1932 | Reisman | 450/154 |
| 3,134,548 | 5/1964 | Medina et al. | 350/98 |
| 3,321,617 | 5/1967 | Santana | 362/103 |
| 3,544,256 | 12/1970 | Feather | 272/143 |
| 3,659,843 | 5/1972 | Kojigian, Jr. | 272/143 |
| 4,112,482 | 9/1978 | Powell | 362/108 |

FOREIGN PATENT DOCUMENTS 1225570  7/1960  France ............................. 128/25 R Primary Examiner—Ira S. Lazarus
Assistant Examiner—David G. Messer
Attorney, Agent, or Firm—Mallinckrodt & Mallinckrodt

[57] ABSTRACT

A belt for joggers, cyclists and other recreationists, having a forwardly shining light to reveal hazards along the path, along with an insulating, sweat producing liner on the body side of the belt, for maximum sweat production for local loss of fatty tissue. The belt also may be worn, at the option of the wearer, in a folded condition without contact of the body with the insulating material, then no longer serving as a sweat generating device.

4 Claims, 3 Drawing Sheets

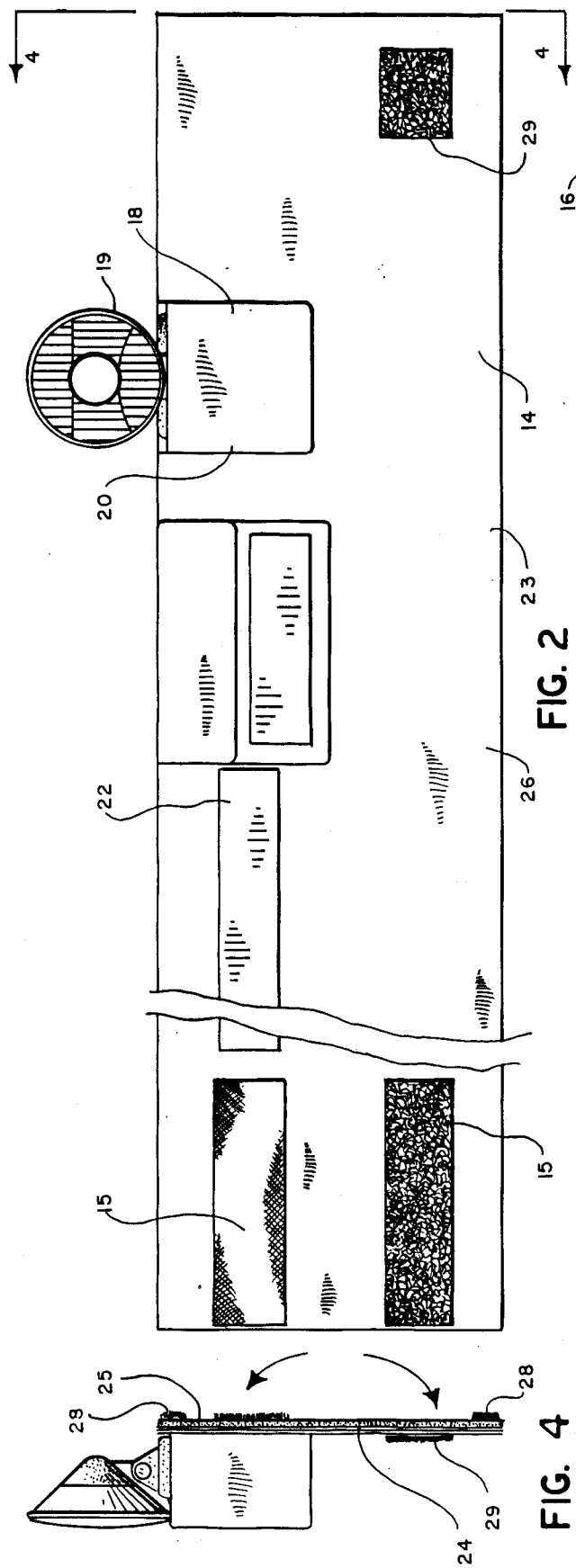
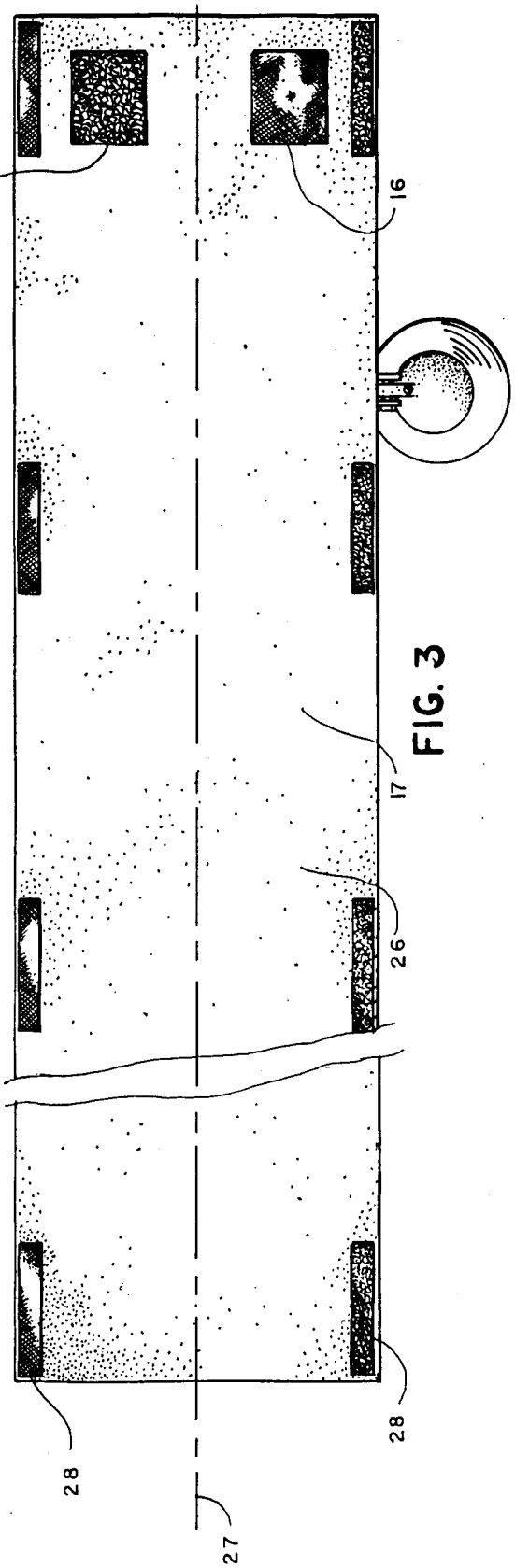

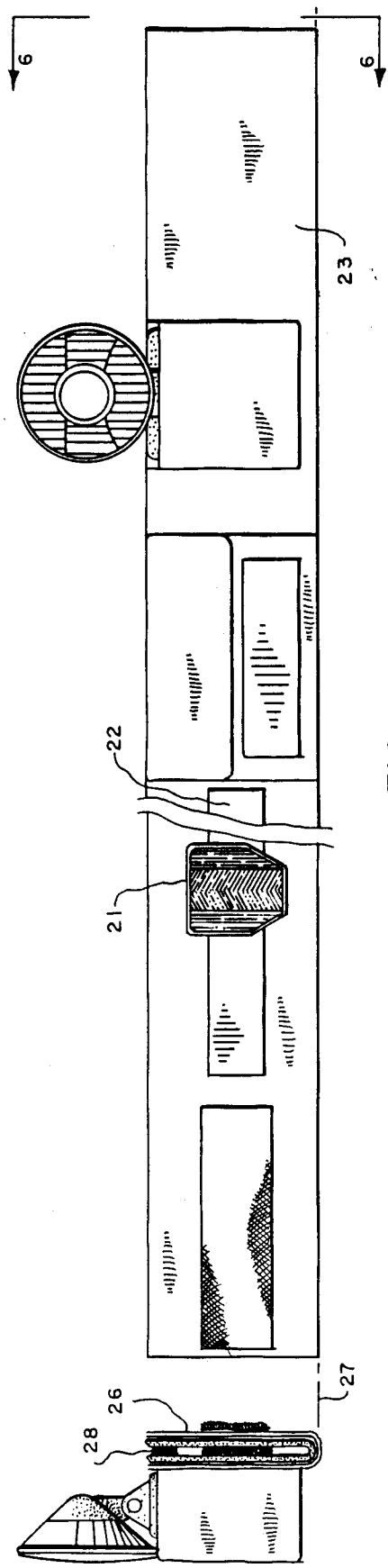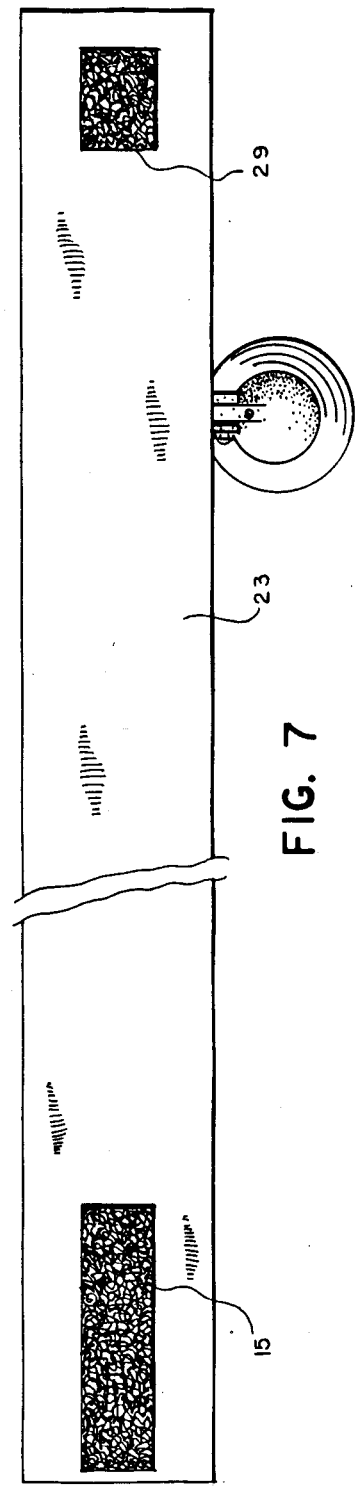

SAFETY LIGHT AND SWEAT BELT

BACKGROUND OF THE INVENTION

Field: The field of the invention is belts to be worn by joggers, cyclists and the like, and more particularly such belts that increase wearer visibility, illuminate the path of travel, and, at the option of the wearer, selectively promote midriff sweating.

State of the Art: Numerous belts have been devised for the use of joggers and cyclists, for example, to increase their visibility and to lessen the danger of occurrence of vehicle-pedestrian accidents. For night use, such belts have been constructed of reflective materials, or reflective tape or glassine reflectors have been appended. Electrically illuminated belts have appeared in various embodiments. Examples include U.S. Pat. Nos. 4,523,258, 4,283,756, and 4,652,981. The last of these includes a flashing light arrangement, enhancing not only visibility but also the noticeability of the wearer to vehicle operators. However, none of these prior art devices has provided illumination to forewarn the wearer of dangerous obstructions such as curbs and pot holes along his path of travel. None of the prior art belts are adapted to serve any basic purposes other than increased visibility and noticeability. For example, none of the belts are designed specifically to promote sweating, believed to aid in reducing unwanted midriff fatty tissues. In fact, most prior art belts are designed to reduce rather than promote such sweating. With prior art belts, considerable danger still remains to the jogger because his path is inadequately visible to him. Benefits from jogging, cycling and the like have therefore been unnecessarily limited because of the shortcomings in belt design.

BRIEF SUMMARY OF THE INVENTION

With the foregoing in mind, the disadvantages and shortcomings in prior art belts for joggers and the like are eliminated or substantially alleviated in the present invention, which provides such a belt comprising a forwardly shining, path illuminating light, which both enhances jogger visibility to motorist and enables the jogger to avoid dangers along his own path. The body side of the belt is covered with a soft, resilient, air impervious insulating material to cause the body to sweat to the maximum degree under the belt. Preferably, the belt is sufficiently wide to substantially cover the midriff, for maximum sweat production. Conversely, at least a portion of the opposing side of the belt is covered with an air breathing material. The belt may, at the option of the wearer, be worn folded with only the cooler, air breathing material in contact with the body.

It is therefore the principal object of the invention to provide an improved belt for joggers and the like, to enhance wearer visibility to vehicle drivers, to illuminate the wearer's path and to serve as an effective sweat inducing device at the option of the wearer.

BRIEF DESCRIPTION OF THE DRAWINGS

In the drawings, which represent the best mode currently contemplated for carrying out the drawings.

DETAILED DESCRIPTION OF ILLUSTRATED EMBODIMENTS

Figure 1:
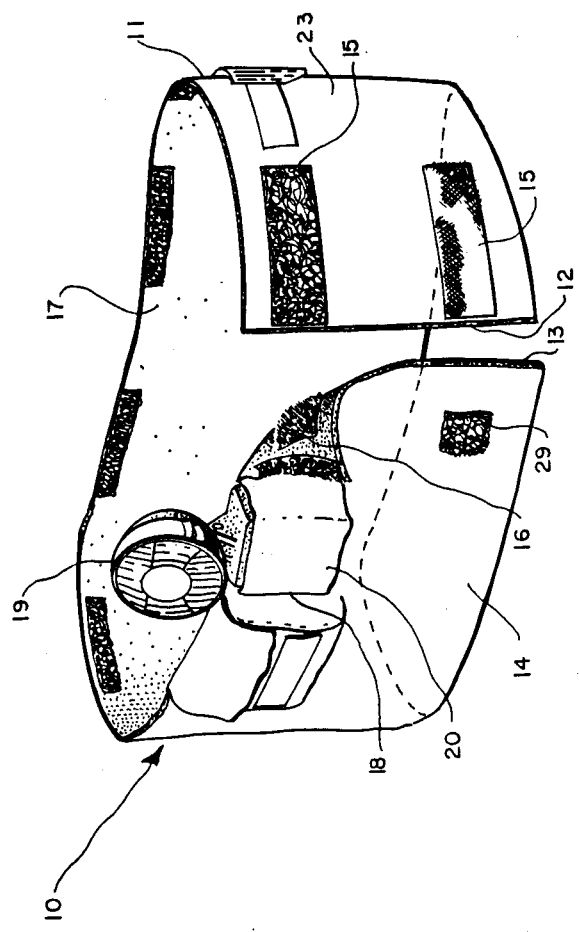
FIG. 1 is a perspective drawing of a jogger's belt in accordance with the invention, depicted in curled configuration as if preparatory to securement about the waist, drawn to a reduced scale, FIG. 2 a front elevation view of representative fragments of the belt of FIG. 1 shown in extended condition, drawn to approximately the scale of FIG. 1, FIG. 3 an inverted rear elevation view of the belt of FIG. 2, drawn to the same scale, FIG. 4 an end elevation view of the belt of FIG. 2 taken along line 4—4 thereof, drawn to the same scale, FIG. 5 a front elevation view of the representative fragments of FIG. 2, the belt thereof, however, being in folded extended condition, drawn to the scale of FIG. 2, FIG. 6 an end elevation view of the folded belt of FIG. 5, taken along line 6—6 thereof, drawn to the same scale, and FIG. 7 an inverted rear elevation view of the belt fragments of FIG. 5, drawn to the same scale.

A safety light and sweat belt 10 is illustrated in the drawings, and comprises an elongate flexible strip 11 to be secured circling the waist of the user. In the illustrated embodiments, "VELCRO" (hook and loop fabric) strips and patches are utilized as fasteners, although buckles, straps and the like could also be used. Strip 11 has inside and outside ends 12 and 13 respectively. (FIGS. 1-4) End 12 carries on its outside surface 14 a pair of elongate strips 15, and end 13 has a matching pair of patches 16 on its inside surface 17. Patches 16 are secured in selective locations along the strips 15 to adjust the belt 10 to the waist.

Carried on the upper half of strip 11 is a forwardly facing, battery powered light 18 comprising a bulb, not shown, and a directional reflector 19. Light 18 may be contained in an upwardly opening pouch 20 secured to project forwardly from outside surface 14. Belt 10 may also carry other aids to night-time visibility, such as reflectors 21, reflective tape strips 22 or other state of the art devices. For example, the outwardly facing surface 14 may be advantageously covered with a reflective cloth 23, such as, "SCOTCHLITE" reflective or luminous material. Reflective tape 22 may be selected from a variety of commercially available colors.

In the illustrated embodiment, belt strip 11 comprises a base of strong fabric 24. Secured to fabric 24 is a layer of insulating material 25. Material 25 is selected for its flexibility and elasticity, softness, and insulative properties, so as to effectively smother the area of the body under belt 10 around the midriff. This is to induce and promote maximum sweating, which is believed to aid in the local loss of fatty tissues. A soft grade of closed cell Neoprene foam has proven very satisfactory, although other materials may be equally effective. The considerable width of belt 10, along with the snug, waist hugging fit provided by the strips 15 and patches 16, eliminates all air circulation between belt 10 and the body, further promoting maximum discharge from the local sweat glands.

To accommodate wearers of belt 10 who may at times not wish to utilize the sweat producing function of belt 10, a portion 26 of strip 11 below longitudinal center line 27, for example, may be secured folded inwardly and upwardly, so that insulating layer 25 is prevented from contacting the body. (FIGS. 3-7) A series of pairs of fold-securing hook and loop patches 28 are provided at intervals along the lower and upper edges of the inside surface 17 of belt 10. An additional hook and loop patch 29 is provided to secure overlapping end 13 to inside end 12, utilizing the upper one of the pair of strips 15.

In this folded configuration, belt 10 has substantially reduced sweat generating properties, both because the body contacting area is reduced, and because the insulating material 25 is prevented from bodily contact. Preferably, outside fabric 23 is selected from air breathing, porous material, for its cooling effect. This need not be incompatible with its reflectivity.

The invention may be embodied in still other specific forms without departing from the spirit or essential characteristics thereof. The present embodiments are, therefore, to be considered as illustrative and not restrictive, the scope of the invention being indicated by the appended claims rather than by the foregoing description, and all changes that come within the meaning and range of equivalency of the claims are, therefore, intended to be embraced therein.

What is claimed and desired to be secured by United States Letters Patent is:

1. A safety light and sweat belt for joggers and the like, comprising:

a strip of flexible material of sufficient length to gird the waist, said strip having a body contacting said and an opposite outwardly facing side and an upper edge and a lower edge;

connecting means for joining the ends of the strip together to secure the belt about the waist;

forwardly directed path illuminating means secured to the belt; wherein the body contacting side of the strip comprises a layer of material having highly insulating properties; and the outwardly facing side of the strop comprises an outermost layer of material having low insulating properties; said belt further comprises;

means releasably securing the upper and lower edges of the belt together to hold the belt in folded condition with the highly insulating layer inside the fold and the low insulating layer on the outside thereof; and connecting means joining the ends of the folded strip together to secure the belt about the waist.

2. The belt of claim 1, wherein:

the path illuminating means comprises a battery powered bulb and associated reflector forwardly directing the light of the bulb.

3. The belt of claim 2, wherein:

the layer of material covering the outwardly facing side of the belt is selected to be highly reflective; and the belt further comprises:

at least one glassine reflector; and at least one strip of reflective tape.

4. The belt of claim 1, wherein:

the layer of material covering the outwardly facing side of the belt is selected to be highly reflective.

* * * * *